US007488297B2

(12) United States Patent
Flaherty

(10) Patent No.: US 7,488,297 B2
(45) Date of Patent: Feb. 10, 2009

(54) BLOOD COLLECTING DEVICES

(76) Inventor: Patrice Flaherty, 1407 County Rd. 3300, Lubbock, TX (US) 79403

( * ) Notice: Subject to any disclaimer, the term of this patent is extended or adjusted under 35 U.S.C. 154(b) by 320 days.

(21) Appl. No.: 11/059,994

(22) Filed: Feb. 17, 2005

(65) Prior Publication Data

US 2006/0009713 A1  Jan. 12, 2006

Related U.S. Application Data

(63) Continuation-in-part of application No. 10/630,402, filed on Jul. 30, 2003.

(51) Int. Cl.
*A61B 5/00* (2006.01)
*A61B 17/32* (2006.01)
*A61B 17/34* (2006.01)
*A61B 19/00* (2006.01)
*B65D 81/00* (2006.01)
*A61H 39/02* (2006.01)
*A61M 37/00* (2006.01)
*A61M 3/00* (2006.01)
*A61M 5/00* (2006.01)
*A61M 25/00* (2006.01)
*A61M 5/32* (2006.01)

(52) U.S. Cl. .................. 600/576; 600/498; 600/573; 600/577; 600/579; 600/580; 606/167; 606/185; 604/6.15; 604/6.1; 604/43; 604/44; 604/45; 604/264; 604/403; 604/411; 604/412

(58) Field of Classification Search .......... 600/498, 600/573, 576, 577, 579, 580; 606/167, 185; 604/6.15, 6.1, 43, 44, 45, 264, 403, 411, 604/412
See application file for complete search history.

(56) References Cited

U.S. PATENT DOCUMENTS

| 3,782,382 A | | 1/1974 | Naftulin et al. | 128/214 R |
|---|---|---|---|---|
| 4,257,416 A | | 3/1981 | Prager | 128/214 R |
| RE31,873 E | | 4/1985 | Howes | 128/674 |
| 4,697,622 A | * | 10/1987 | Swift et al. | 141/1 |
| 4,701,160 A | | 10/1987 | Lindsay et al. | 604/53 |
| 5,084,034 A | | 1/1992 | Zanotti | 604/319 |
| 5,203,771 A | | 4/1993 | Melker et al. | 604/53 |
| 5,364,377 A | | 11/1994 | O'Neil | 604/283 |
| 5,486,159 A | | 1/1996 | Mahurkar | 604/4 |
| 5,653,686 A | * | 8/1997 | Coulter et al. | 222/1 |
| 5,746,724 A | * | 5/1998 | Powles et al. | 604/240 |
| 5,795,340 A | | 8/1998 | Lang | 604/283 |
| 6,235,010 B1 | * | 5/2001 | Wilkinson et al. | 604/356 |
| 6,379,340 B1 | * | 4/2002 | Zinger et al. | 604/246 |
| 6,508,778 B1 | | 1/2003 | Verkaart et al. | 604/6.15 |

* cited by examiner

*Primary Examiner*—Max Hindenburg
*Assistant Examiner*—Jeffrey G Hoekstra
(74) *Attorney, Agent, or Firm*—R Keith Harrison

(57) ABSTRACT

Blood collecting devices for collecting blood from a patient using a single needle insertion are disclosed. Each blood collecting device typically includes a housing which is removably attached to a test tube or blood reservoir. A blood flow tube is disposed in fluid communication with the housing for distributing blood from a patient into the test tube or blood reservoir. The blood is distributed through a membrane cavity having a liquid-impervious and air-permeable membrane. At least one air opening is provided in the housing at the membrane cavity. Accordingly, air in the test tube or blood reservoir is displaced by the incoming blood through the membrane cavity and membrane and out the air opening or openings. Vacuum pressure in the test tube or blood reservoir is dispelled by the flow of air through the air opening or openings, membrane cavity and membrane and into the test tube or blood reservoir, respectively.

6 Claims, 8 Drawing Sheets

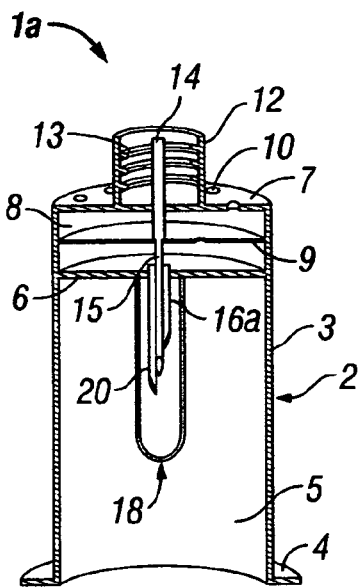
FIG. 6
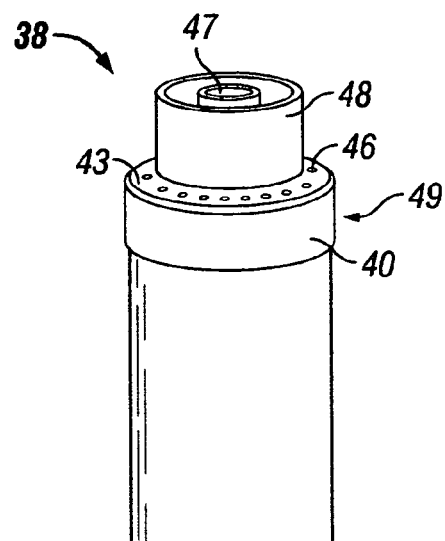
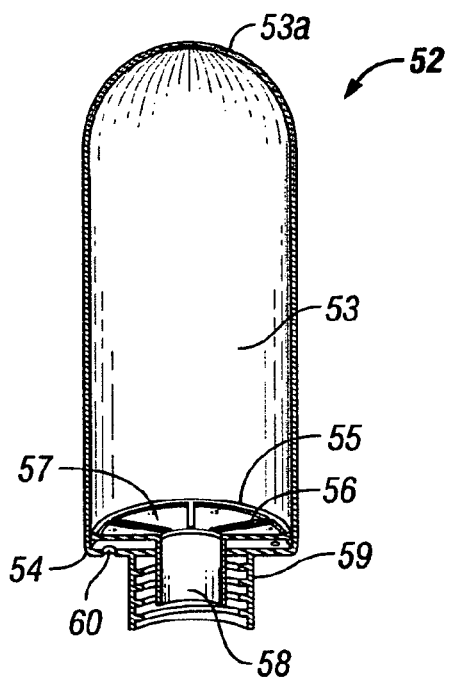
FIG. 9
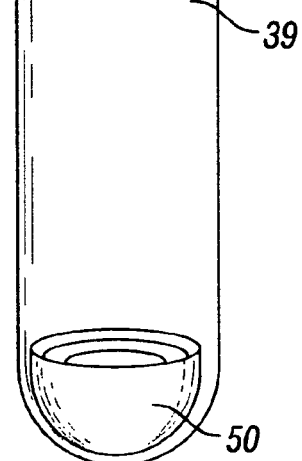
FIG. 7

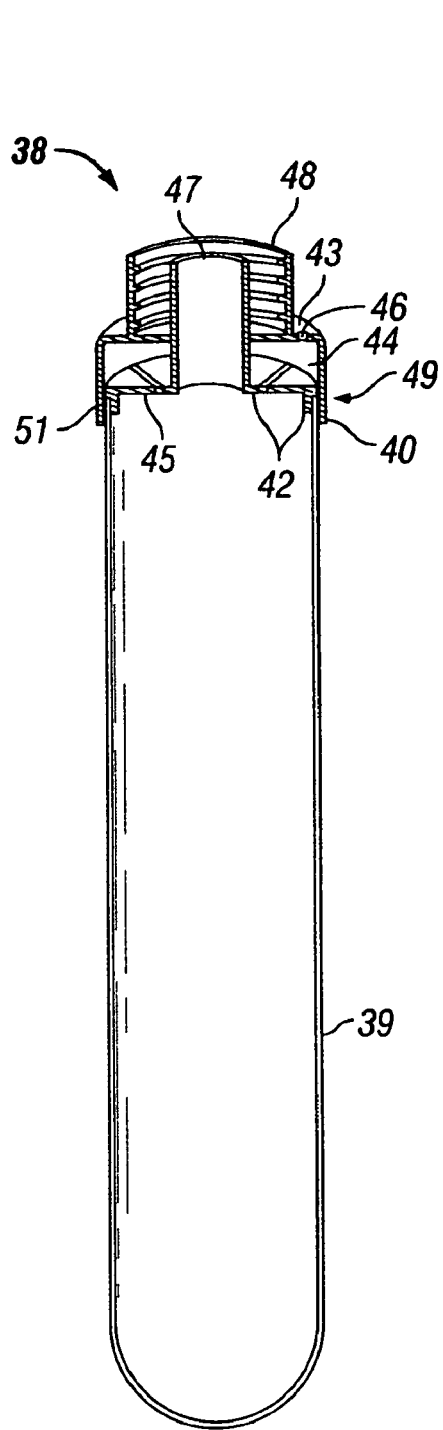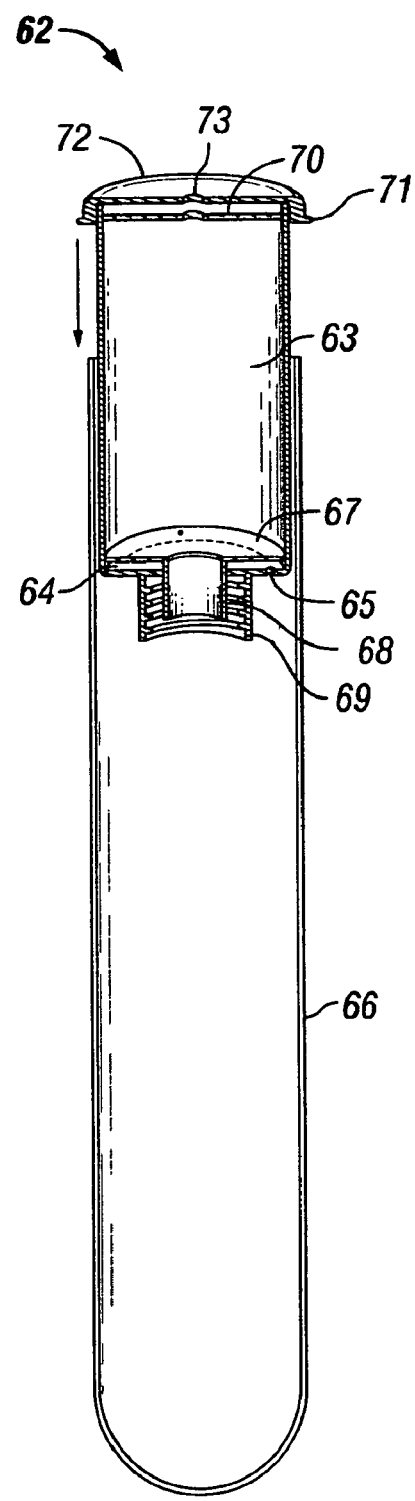
FIG. 8
FIG. 10

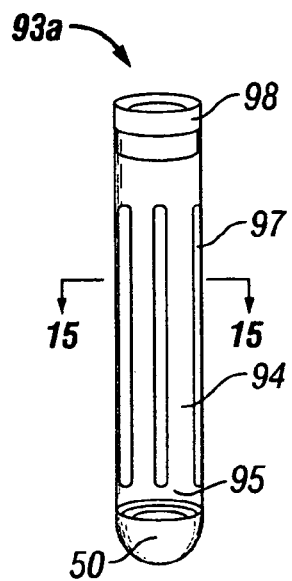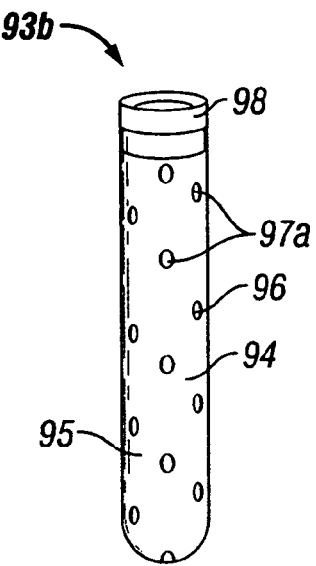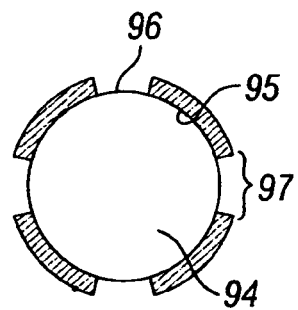
FIG. 14A  FIG. 14B  FIG. 15
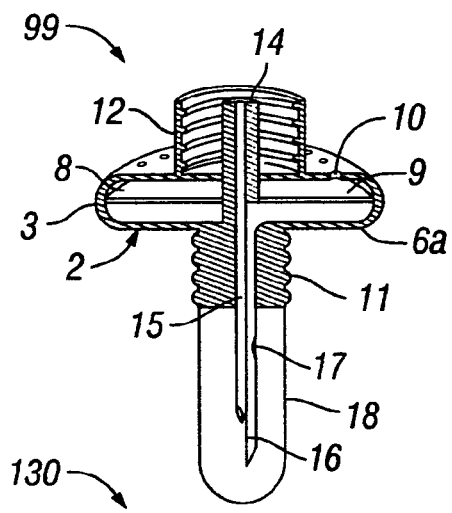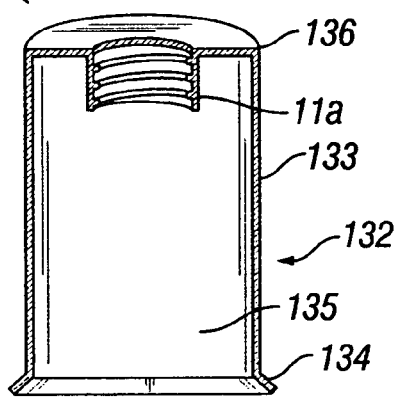
FIG. 16

BLOOD COLLECTING DEVICES

CROSS-REFERENCE TO RELATED APPLICATIONS

This application is a continuation-in-part of application Ser. No. 10/630,402, filed Jul. 30, 2003, which application is herein incorporated by reference in its entirety.

FIELD OF THE INVENTION

The present invention relates to syringes and other devices for removing blood from a patient. More particularly, the present invention relates to novel blood collecting devices which can be used to collect blood from a patient using a single needle insertion.

BACKGROUND OF THE INVENTION

Patients who undergo medical treatment in hospitals frequently require both extraction of blood for blood testing purposes and intravenous administration of medical fluids. Proper treatment of the patient may require that the blood be extracted and the medical fluids administered repeatedly and on a regular basis. In the past, this procedure has required that multiple needle insertions be made in various locations of the patient's body to access veins such as the external or internal jugular, subclavian, cephalic, femoral or saphenous veins. Multiple needle insertions not only result in considerable discomfort to the patient but also increase the risk of infection and compound the danger that medical personnel will be pricked by a contaminated needle.

Conventional methods of drawing blood from a patient typically utilize partial vacuum pressure to draw the blood from one of the patient's veins into a collecting device. Such utilization of partial vacuum pressure to draw blood from the vein tends to prematurely collapse the vein, thus necessitating re-insertion of the collecting device in another vein or in the same vein at a separate location to draw additional blood. This problem is particularly common in the drawing of blood from infants and the aged, in which small, thin veins are typically the source for blood samples. Accordingly, a device is needed which facilitates collection of blood from a patient on a repeated basis using one, rather than multiple, needle insertions and which prevents premature collapse of a vein by utilizing intrinsic venous blood pressure to collect blood.

SUMMARY OF THE INVENTION

The present invention is generally directed to novel blood collecting devices for collecting blood from a patient using a single needle insertion. Generally, the blood collecting devices include a housing which is removably attached to a test tube or blood reservoir. A blood flow tube is disposed in fluid communication with the housing for distributing blood from a patient into the test tube or blood reservoir. The blood passes through a membrane cavity having a liquid-impervious and air-permeable membrane, and at least one air opening is provided in the housing at the membrane cavity. Accordingly, as the blood enters the test tube or blood reservoir, air is displaced through the membrane cavity and membrane and out the air opening or openings. Prior to collection of blood, vacuum pressure in the test tube or blood reservoir is dispelled by the flow of air into the test tube or blood reservoir through the air opening or openings, membrane cavity and membrane and into the test tube or blood reservoir, respectively.

BRIEF DESCRIPTION OF THE DRAWINGS

The invention will now be described, by way of example, with reference to the accompanying drawings, in which:

FIG. 6 is a cross-sectional view of a second embodiment of the blood collecting devices of the present invention;

FIG. 7 is a perspective view of a third embodiment of the blood collecting devices of the present invention, removably attached to a test tube illustrating a blood testing reagent provided in the bottom of the test tube;

FIG. 8 is a longitudinal cross-sectional view of the blood collecting device of FIG. 7;

FIG. 9 is a longitudinal cross-sectional view of a fourth embodiment of the blood collecting devices;

FIG. 10 is a longitudinal cross-sectional view of a fifth embodiment of the blood collecting devices inserted in an uncapped conventional test tube;

FIG. 14A is a perspective view of a seventh embodiment of the blood collecting device;

FIG. 14B is an alternative to the blood collecting device shown in FIG. 14A;

FIG. 15 is transverse sectional view of the blood collecting device shown in FIG. 14A;

FIG. 16 is a cross-section of eight embodiment of the blood collecting device;

DETAILED DESCRIPTION OF THE INVENTION

The present invention is generally directed to novel blood collecting devices for collecting blood from a patient using a single needle insertion. The devices facilitate the collection of venous blood from a patient using the venous pressure of the blood, preventing vacuum-induced collapsing of the vein. As used herein, relative terms such as "upper" and "lower" shall not be construed to limit the positions of the device components in a functioning device but are used to indicate the relative positions of the components with respect to each other in the device when the device is in the vertical position.

Figure 1:
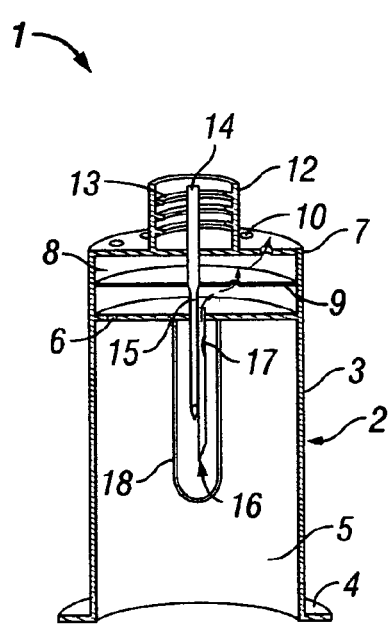
FIG. 1 is a cross-sectional view of a first embodiment of the blood collecting devices of the present invention.
Figure 2:
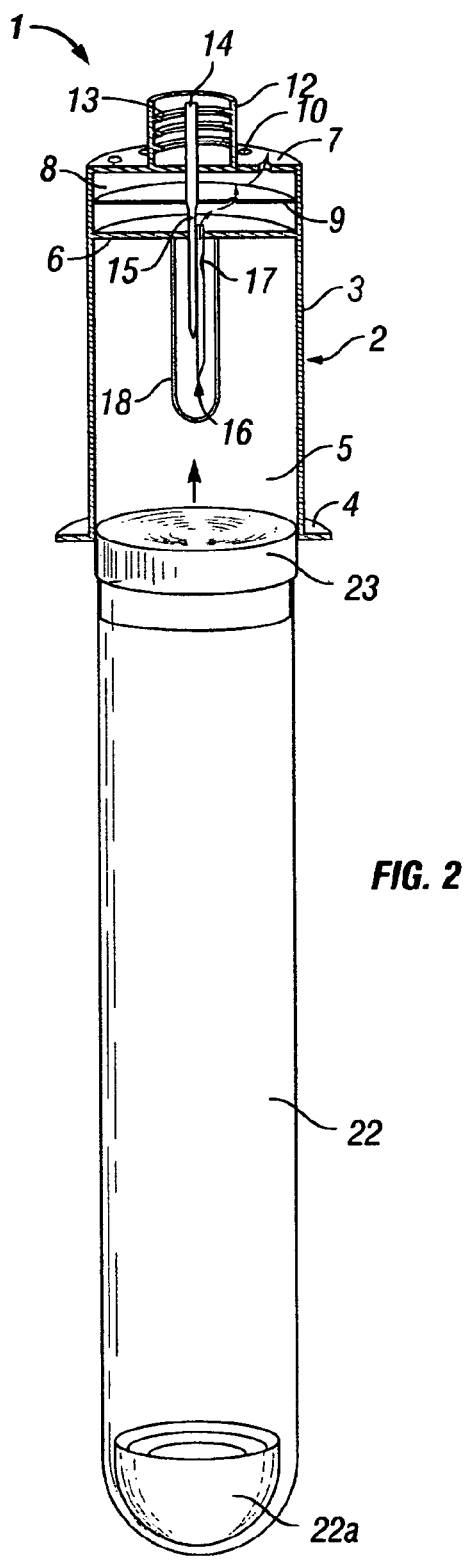
FIG. 2 is a side view illustrating typical insertion of the blood collecting device (shown in section) of FIG. 1 on a capped test tube illustrating a blood-testing reagent provided in the bottom of the test tube.

Referring initially to FIGS. 1 and 2 of the drawings, a first illustrative embodiment of the blood collecting devices of the present invention is generally indicated by reference numeral 1. As illustrated in FIG. 2 and hereinafter described, a test tube 22 having a stopper 23 is adapted to be removably inserted into the blood collecting device 1. The test tube 22 may be conventional and is typically a vacuum test tube in which the stopper 23 maintains a vacuum pressure inside the test tube 22. Various reagents 22a may be included in the test tube 22 for blood-testing purposes, as is known by those skilled in the art. The blood collecting device 1 includes a housing 2 which may be plastic and includes a generally cylindrical housing wall 3. An annular housing flange 4 typically flares outwardly from the bottom end of the housing wall 3. A lower housing plate 6 spans the housing wall 3, inside the housing interior 5. An upper housing plate 7 is provided on the housing wall 3, above and in spaced-apart relationship to the lower housing plate 6. At least one air opening 10, the purpose of which will be hereinafter described, extends through the upper housing plate 7. A membrane cavity 8 is defined between the lower housing plate 6 and the upper housing plate 7. A membrane 9, which is a liquid-impenetrable and air-permeable material, spans the housing wall 3 in the membrane cavity 8. A self-sealing needle shield 18, which may be a self-sealing rubber or plastic, for example, extends downwardly from the lower surface of the lower housing plate 6, into the housing interior 5.

A male luer connector 12 having interior connector threads 13 extends from the upper housing plate 7. A blood flow tube 14 extends from the upper housing plate 7, through the center of the male luer connector 12 and below the membrane 9. A blood flow needle 15, which may be a cannulated needle (as shown) or a blunt plastic tube, communicates with the blood flow tube 14 and extends downwardly from the blood flow tube 14. The blood flow needle 15 extends downwardly through the lower housing plate 6, respectively, and terminates within the needle shield 18. An air flow needle 16, which may be a cannulated needle (as shown) or a blunt plastic tube, is attached to one side of the blood flow needle 15. The lower end of the air flow needle 16 terminates below the lower end of the blood flow needle 15, within the needle shield 18. The upper end of the air flow needle 16 extends through the lower housing plate 6, adjacent to the blood flow needle 15, and terminates in the membrane cavity 8, beneath the membrane 9. Preferably, an air opening 17 is provided in the side of the air flow needle 16, beneath the lower housing plate 6 and above the lower opening of the blood flow needle 15. In the embodiment of the blood collecting device 1 in which the blood flow needle 15 and air flow needle 16 are blunt plastic tubes, the needle shield 18 may be omitted. Alternatively, the needle shield 18 may be included in the blood collecting device 1, in which case a slit (not illustrated) is provided in the needle shield 18 to permit passage of the blunt tubes therethrough.

Figure 17:
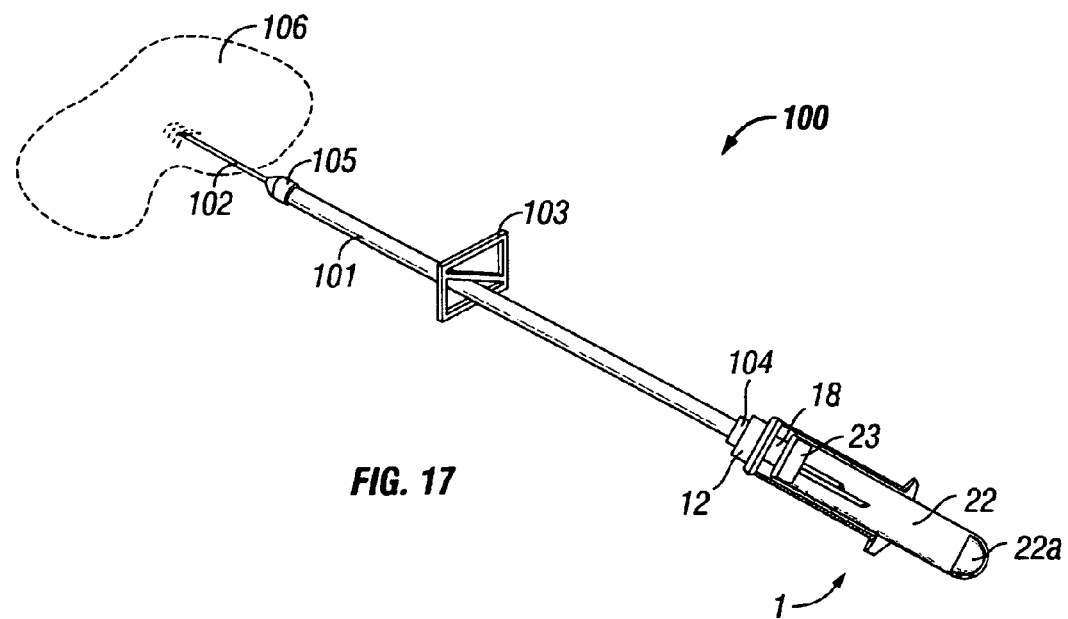
FIG. 17 is a perspective view of a blood collection tubing, with the blood collecting device of FIG. 1 and FIG. 2 attached to the tubing for the collection of blood from a patient (in phantom)

Referring next to FIGS. 2 and 17, in typical application, the blood collecting device 1 is designed to facilitate the collection of blood from a patient 106 (shown in phantom in FIG. 17) through a blood collection tubing 100. However, it is understood that the blood collecting device 1 may be used in conjunction with any type of catheter or I.V. tubing which is adapted to collect blood from a patient. The blood collection tubing 100 includes a main tubing segment 101 having a male luer connector 105 which is attached a cannula 102 that has been inserted in the patient 106. The main tubing segment 101 may be fitted with a clamp 103 which is preferably capable of one-handed operation. A port 104, which is typically a needle-less female port, but which alternatively may be needle-protected, is attached to collection tubing segment 101. The port 104 may be a male threaded port, a female threaded port or any type of connection port to facilitate connection with the collection tubing segment 101.

Referring to FIGS. 1, 2, and 17, in operation, the I.V. cannula 102 is initially inserted in a vein in the patient 106. With the clamp 103 in the open position, the male luer connector 105 of the tubing 101 is attached to the hub of the catheter 102. Next the male luer 12 of the blood collection device 1 is attached to the collection tubing segment 101 at the port 104. As illustrated in FIG. 2, the test tube 22, with the stopper 23 remaining in place, is inserted into the housing interior 5 of the blood collecting device 1. Accordingly, the air flow needle 16 and blood flow needle 15, respectively, are inserted through the needle shield 18 and rubber stopper 23, respectively, and extend into the test tube 22 as the needle shield 18 is impaled on the air flow needle 16 and blood flow needle 15, causing needle shield 18 to be compressed between stopper 23 and the lower plate 6. Consequently, vacuum pressure in the test tube 22 is released by outside air flowing into the test tube 22 through the air opening 10, membrane 9 and air flow needle 16, respectively. Blood then flows under venous pressure from the patient 106 and through the cannula 102, collection tubing segment 101, central blood flow tube 14 and blood flow needle 15, respectively, of the blood collecting device 1, into the test tube 22.

As illustrated in FIG. 2, as blood enters the test tube 22, air is displaced from the test tube 22 through the air flow needle 16, the air-permeable membrane 9 and the air opening 10, respectively, allowing blood to flow at the venous pressure. In the event that blood covers the distal hole in the air flow needle 16, air can escape from the test tube 22 by flowing into the air flow needle 16 through the air opening 17, and then from the blood collecting device 1 through the membrane 9 and air opening 10, respectively. Additionally, if the distal opening in the air flow needle 16 is occluded with blood, air preferentially flows through the air opening 17 in the air flow needle 16, preventing blood from being pulled upwardly through the air flow needle 16 and into the portion of the membrane cavity 8 beneath the membrane 9, thus stopping flow of the air and preventing further extraction of blood from the patient 106.

After the desired sample of blood has been collected from the patient 106 into the test tube 22, this tube may be replaced by an empty tube for additional samples. When withdrawal of blood is completed, tubes may be centrifuged and subjected to various blood tests. As the blood-filled test tube 22 is removed from the blood collecting device 1, the needle shield 18 will extend over the blood flow needle 15 and air flow needle 16 to again contain the blood flow needle 15 and air flow needle 16. The needle shield 18 is self-sealing to prevent leakage of blood which remains in the blood flow needle 15 from the blood collecting device 1. The male luer connector 12 on the blood collecting device 1 can then be detached from the port 104 of the blood collection tubing 101. After the blood collecting device 1 is discarded and the blood collection tubing 101 is flushed with saline solution, the blood collection tubing 101 can be used as any ordinary I.V. tubing.

Figure 3:
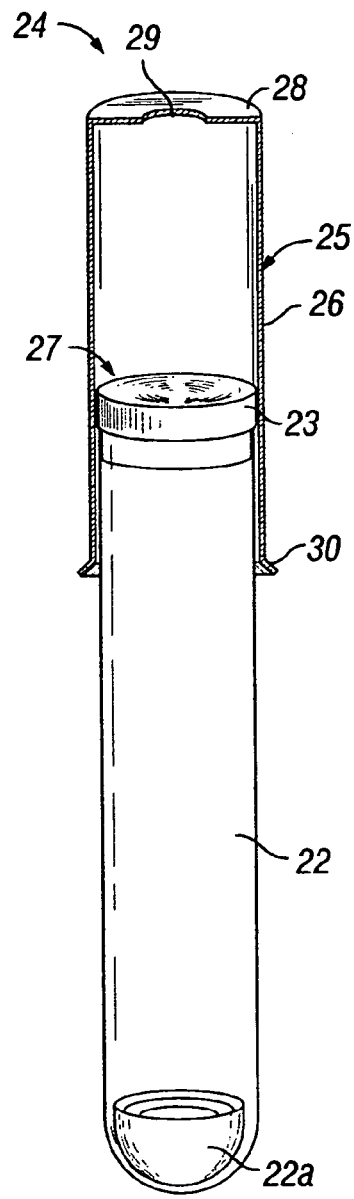
FIG. 3 is a cross-section of a test tube guide sleeve used to guide a capped test tube during insertion of the blood collecting device on the test tube.

Referring next to FIG. 3 of the drawings, a test tube guide sleeve 24 which may be used to guide a small or low-volume test tube 22 into the housing interior 5 (FIG. 1) of the blood collecting device 1 for piercing of the stopper 23 by the blood flow needle 15 and air flow needle 16 is illustrated. The test tube guide sleeve 24 includes a sleeve housing 25 having a typically cylindrical housing wall 26 which defines a housing interior 27. A typically circular housing plate 28, having a central housing opening 29, is provided on the upper end of the housing wall 26. A housing flange 30 may flare outwardly from the lower end of the housing wall 26. In use, the sleeve housing 25 is initially inserted into the housing interior 5 (FIG. 1) of the blood collecting device 1. The housing flange 30 is sized to cause the guide sleeve to be centered within housing interior 5. The needle shield 18 and the enclosed needles 15 and 16 then protrude through the central housing opening 29 into the housing interior 27. The upper end of the test tube 22, with the stopper 23 inserted therein, is inserted into the housing interior 27 until the stopper 23 abuts against the inner surface of the housing plate 28, such that the air flow needle 16 and blood flow needle 15, respectively, pierce the needle shield 18 the stopper 23 and enter the test tube 22, respectively.

Figure 4:
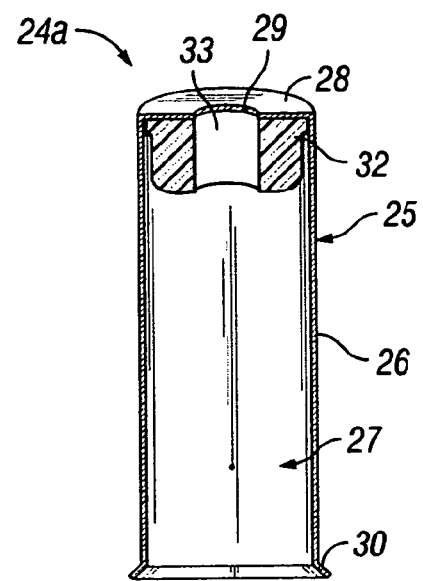
FIG. 4 is a cross-section of another embodiment of the test tube guide sleeve for guiding an uncapped test tube during insertion of the blood collecting device on the test tube.

An alternative embodiment of the test tube guide sleeve 24a is illustrated in FIG. 4. The test tube guide sleeve 24a can be used with the embodiment of the blood collecting device 1 in which the blood flow needle 15 and air flow needle 16 are blunt plastic tubes rather than cannulated needles. Furthermore, the test tube guide sleeve 24a can be used with test tubes 22 in which the stopper 23 is incapable of being pierced by the blood flow needle 15 and the air flow needle 16, and therefore, must be removed from the test tube 22 before use of the blood collecting device 1. An interior projection 32, which may be rubber or plastic, for example, is provided in the upper portion of the housing interior 27, against the interior surface of the housing plate 28. A cap opening 33 extends through the interior projection 32 and communicates with the housing opening 29 in the housing plate 28. In use of the test tube guide sleeve 24a, the sleeve housing 25 is initially inserted into the housing interior 5 (FIG. 1) of the blood collecting device 1. The stopper 23 is removed from the test tube 22, and the upper end of the uncapped test tube 22 is inserted into the housing interior 27 until the upper end of the test tube 22 fits firmly around the interior projection 32, such that the blunt plastic air flow tube 16 and blood flow tube 15, respectively, extend through the housing opening 29 of the housing plate 28 and then through the cap opening 33 of the interior projection 32 and into the uncapped test tube 22, respectively. The blood collecting device 1 is used as described hereinabove with respect to FIG. 17. When a sufficient sample of blood is collected in the test tube 22, the clamp 103 (FIG. 17) is manipulated to close the blood collection tubing 101, causing the blood flow to stop. Additional samples can be collected by replacing the test tube 22 and opening the clamp 103.

Figure 5:
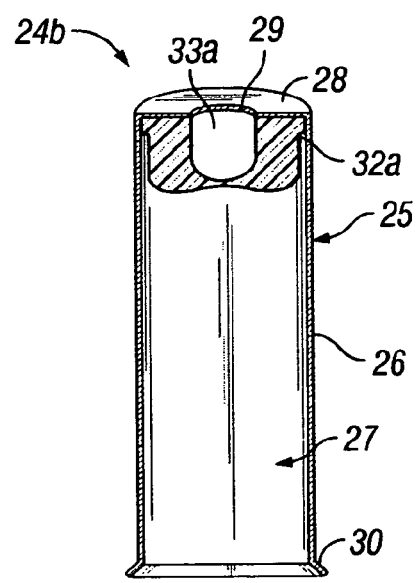
FIG. 5 is a cross-section of still another embodiment of the test tube guide sleeve for guiding an uncapped test tube during insertion of the blood collecting device on the test tube.

Another alternative embodiment of the test tube guide sleeve 24b is illustrated in FIG. 5 and is suitable for use with the embodiment of the blood collecting device 1 in which the blood flow needle 15 and air flow needle 16 are cannulated and the needle shield 18 covers the blood flow needle 15 and air flow needle 16. Furthermore, the test tube guide sleeve 24b can be used with test tubes 22 in which the stopper 23 is incapable of being pierced by the blood flow needle 15 and the air flow needle 16, and therefore, must be removed from the test tube 22 before use of the blood collecting device 1. The interior projection 32a, rather than having the cap opening 33 extending therethrough as with the test tube guide sleeve 24a of FIG. 4, is of a self-sealing material with thinned area firm enough to push back needle shield 18. Accordingly, the stopper 23 is initially removed from the test tube 22, which is then extended into the housing interior 27 of the test tube guide sleeve 24b. The test tube guide sleeve 24b is then inserted into the housing interior 5 of the blood collecting device 1, such that the blood flow needle 15 and air flow needle 16 extend through the housing opening 29 of the housing plate 28 and the interior projection 32A, respectively, and into the test tube 22.

Referring next to FIG. 6 of the drawings, an alternative embodiment of the blood collecting device 1a of the present invention includes a puncturing needle 20 which is typically attached to one side of the blood flow needle 15. The upper end of the puncturing needle 20 typically extends through the lower housing plate 6 and opens into the membrane cavity 8, beneath the membrane 9. An air flow needle 16a, which is similar in design to the air flow needle 16 of the embodiment heretofore described with respect to FIG. 1, except lacks the air opening 17, is attached to the opposite side of the blood flow needle 15. The upper end of the air flow opening 16a is located in the membrane cavity 8 below the membrane 9. Accordingly, during insertion of the test tube 22 into the housing interior 5, the puncturing needle 20 punctures the needle shield 18 and stopper 23 in the test tube 22, respectively. This relieves the vacuum pressure in the test tube 22 by facilitating the flow of air through the air opening 10, membrane 9 and puncturing needle 20, respectively, into the test tube 22. Blood then flows into test tube 22 as described in FIG. 1.

Referring next to FIGS. 7 and 8 of the drawings, still another embodiment of the blood collecting device is generally indicated by reference numeral 38. The blood collecting device 38 includes a blood collection chamber 39 and a cap 49 which is removably fitted on the blood collection chamber 39 typically via a friction-fit or threads. The bottom of the blood collection chamber 39 is preferably shaped in the convex configuration of a standard test tube. As illustrated in FIG. 7, the blood collection chamber 39 may contain a reagent or separation gel 50 or be coated with a reagent, such as heparin or EDTA (ethylene diamine tetra-acetic acid), for example, to facilitate testing of blood collected in the blood collection chamber 39, as will be hereinafter described. As further illustrated in FIG. 8, the cap 49 includes a housing 40 having a generally cylindrical shape. The lower end of the housing 40 defines a housing flange 51 which may be adapted to engage the upper end of the blood collection chamber 39 in a friction-fit. Alternatively, the housing flange 51 may be provided with interior or exterior threads (not illustrated) which engage companion exterior or interior threads (not illustrated), respectively, on the blood collection chamber 39. An upper housing plate 43 is provided on the upper end of the housing wall 40. A liquid impenetrable, air-permeable membrane 45 spans the housing wall 40, held in place by a membrane support 42. A membrane cavity 44 is defined between the membrane 45 and the upper housing plate 43. At least one air opening 46 extends through the upper housing plate 43. As shown in FIG. 7, multiple air openings 46 may extend through the upper housing plate 43. Accordingly, due to the presence of the air permeable membrane 45, and the air opening or openings 46 in the upper housing plate 43, no vacuum pressure is ever present in the blood collection chamber 39. A male luer connector 48 extends upwardly from the upper housing plate 43. A blood flow tube 47 extends centrally through the male luer connector 48 and extends downwardly through the center of the upper housing plate 43, the membrane 45 and the membrane support 42. The blood flow tube 47 is typically connected to the lower membrane support 42 and the upper housing plate 43.

In use, the blood collecting device 38 may be used in conjunction with the blood collection tubing 100 (FIG. 17)

which was heretofore described with respect to FIG. 1. Accordingly, the cap 49 is initially fitted on the blood collection chamber 39. The cannula 102 is inserted in the patient 106, and the tubing 101, with the clamp 103 in open position, is attached and taped in place. The male luer connector 48 of the cap 49 is attached to the port 104 of the blood collection tubing 101. Blood then flows from the patient 106 and through the cannula 102, main tubing segment 101, and into the blood collection chamber 39 through the blood flow tube 47. As blood flows into the blood collection chamber 39, air is displaced from the blood collection chamber 39, through the membrane 45 and air opening or openings 46, respectively. This facilitates the substantially continual and unhindered flow of blood from the patient 106 and into the blood collection chamber 39 to collect the desired quantity of blood into the blood collection chamber 39. It is understood that the blood collecting device 38, without reagent 50, can be used in conjunction with tubing 110 of FIG. 18, in the manner which will be hereinafter described with respect to other embodiments of the blood collecting device.

After the desired quantity of blood from the patient 106 has been collected in the blood collection chamber 39, the clamp 103 may be manipulated to the closed position to prevent further flow of blood in the main tubing segment 101. The male luer connector 48 on the blood collecting device 38 is then disconnected from the port 104 on the blood collection tubing 101. With the cap 49 typically remaining in place on the blood collection chamber 39, the blood collection chamber 39 may then be placed in a centrifuge (not illustrated) to separate red blood cells from plasma for analysis. Additional or alternative blood testing may be accomplished by using a blood transfer device (not shown) to remove blood from within the tube or removing the cap 49 from the blood collection chamber 39 to remove the blood therefrom. While use of the cap 49 has been heretofore described in conjunction with the blood collection chamber 39, it will be appreciated by those skilled in the art that with little or no modification, the cap 49 can be used with a standard test tube, such as the test tube 22 heretofore described with respect to FIG. 2.

Referring next to FIG. 9 of the drawings, yet another embodiment of the blood collecting device is generally indicated by reference numeral 52 and includes a blood reservoir 53. The bottom 53a of the blood reservoir 53 is preferably a convex shape, such as that of a test tube. A reservoir plate 54 closes the upper end of the blood reservoir 53. At least one air opening 60 extends through the reservoir plate 54. A blood flow tube 58 extends from the reservoir plate 54, and a male luer connector 59 extends from the reservoir plate 54 and encircles the blood flow tube 58. An annular membrane frame 55 is provided in the blood reservoir 53 and is spaced-apart with respect to the reservoir plate 54. An annular, liquid-impenetrable, air-permeable membrane 57 is mounted on the membrane frame 55. Frame ribs 56 may extend inwardly from the membrane frame 55 to support the membrane 57. The blood flow tube 58 is disposed in fluid communication with the blood reservoir 53 passing through the center of membrane frame 55 and ribs 56.

In use, a male luer 116 of a device 110 (FIG. 18), which is described in detail in U.S. patent application Ser. No. 10/630, 402, filed Jul. 30, 2003, is attached at the hub of a catheter 121 with a clamp 120 in open position. The male luer connector 59 of the blood collecting device 52 is connected to the female needle-less port 123 of the blood collection tubing 110 (FIG. 18) or other catheter or I.V tubing (not illustrated). As blood flows from the patient 122 (FIG. 18), blood collection tubing 111, bifurcation 117, branch tubing 112, blood flow tube 58 and into the blood reservoir 53, respectively, air displaced by the blood flows from the blood reservoir 53, through the membrane 57 (FIG. 9) and out the air opening 60, respectively. Pressure within the blood reservoir 53 remains at ambient air pressure and less than venous pressure, facilitating the flow of blood from patient 122 into the blood reservoir 53 under the venous blood pressure. Next a syringe 115 may be attached on a female port 114 of the blood collection tubing 110. Withdrawing on the plunger of the syringe 115 causes blood to flow from blood collection device 52 through collection tubing segment 112, around tubing bifurcation 117, and collection tubing 113, respectively, and enters the syringe 115. Alternatively, a blood collection tube holder (not shown) may be attached at female port 114 and an evacuated tube (not shown) may be inserted to extract the blood from the blood collection device 52. Sufficient blood must be in blood collection device 52 for a good sample to be obtained, or air will be pulled into the evacuated tube from the blood collection device 52. After sufficient blood is collected, the clamp 120 is manipulated to the closed position and a syringe 115 filled with normal saline is attached to the female port 114. The tubing segment 113, tubing bifurcation 117 and tubing segment 112 are flushed with normal saline and the blood collection device 52 is discarded. The clamp 120 is then opened and the tubing segment 111 flushed as the saline flows into the patient 122. The syringe 115 or blood collection tube holder with an evacuated tube (not shown) is removed and the device 110 is used as ordinary extension tubing. However, it is understood that the blood collecting device 52 may be used in conjunction with any type of catheter or I.V. tubing which is adapted to collect blood from a patient, such as the blood collection tubing 100 of FIG. 17, for example.

Referring next to FIG. 10, a still further embodiment of the blood collecting device 62 of the present invention includes a blood reservoir 63. A reservoir plate 64 closes the upper end of the blood reservoir 63. At least one, and typically, multiple air openings 65 extend through the reservoir plate 64. A blood flow tube 68, which is provided in fluid communication with the blood reservoir 63, and a male luer connector 69 extend from the reservoir plate 64. An annular membrane 67, which is liquid impenetrable and air-permeable, is provided in the blood reservoir 63, against the reservoir plate 64. The membrane 67 covers that portion of the reservoir plate 64 which extends outwardly beyond the male luer connector 69 and has the air openings 65. A second liquid impenetrable, air-permeable membrane 70 may be provided in the lower end of the blood reservoir 63. An annular flange 71 extends outwardly from the blood reservoir 63 and encircles the membrane 70, and may be enclosed in a plastic housing 72. At least one air opening 73 extends through the plastic housing 72.

In use, the blood collecting device 62 is connected to the blood collection tubing 110 (FIG. 18) to collect blood from a patient 122, typically in the manner heretofore described with respect to the blood collection device 52 of FIG. 9. After collection of the blood in the blood reservoir 63 is completed, the blood collecting device 62 is disconnected from the blood collection tubing 110. The blood flow tube 68 end of the blood collecting device 62 is then inserted in a test tube 66, with the flange 71 of the blood collecting device 62 engaging the mouth of the test tube 66. Accordingly, the test tube 66 can then be placed in a centrifuge (not illustrated) to separate blood cells from plasma in the test tube 66. During centrifuging, the blood exits the blood reservoir 63 and enters the test tube 66, where the blood cells are separated from the plasma.

Figure 11:
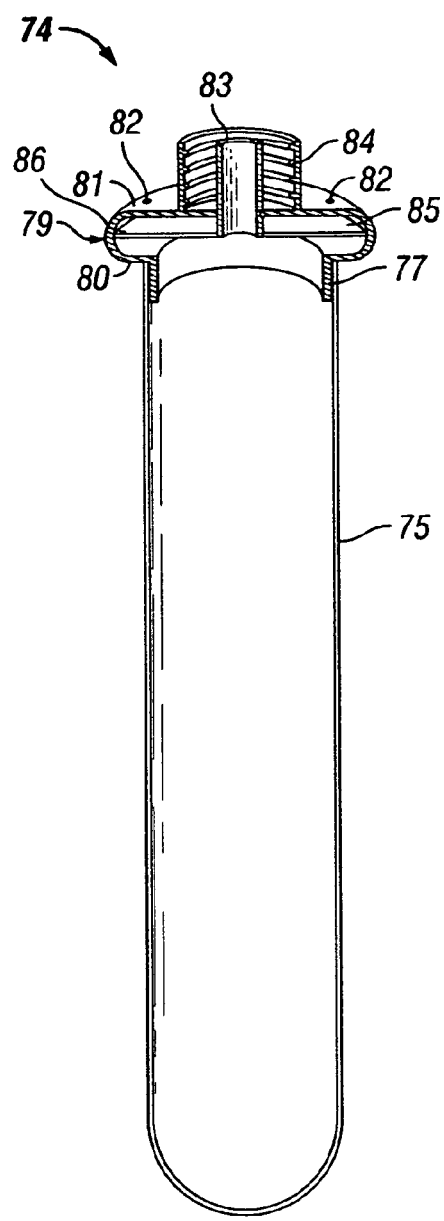
FIG. 11 is a cross-sectional view of a sixth embodiment of the blood collecting devices, mounted on a test tube.

Referring next to FIG. 11, another embodiment of the blood collecting device 74 which forms a cap adapted to be removably fitted on a test tube 75 is illustrated in FIG. 11. The cap 74 includes an annular cap base 77 which is capable of insertion into the mouth of the test tube 75. A cap housing 79 flares outwardly from the cap base 77 and includes a lower housing plate 80 and an upper housing plate 81 which define a membrane cavity 85. An annular, liquid-impenetrable, and air-permeable membrane 86 is provided in the membrane cavity 85. At least one, and typically, multiple air openings 82 are provided in the upper housing plate 81. A blood flow tube 83 extends centrally through the upper housing plate 81 and membrane 86. A male luer connector 84 extends from the upper housing plate 81 and encircles the blood flow tube 83.

Figure 12:
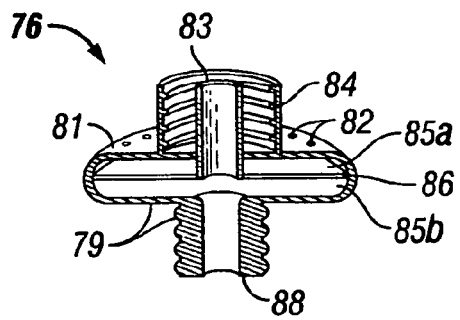
FIG. 12 is an exploded view of a seventh embodiment of the blood collecting device.
Figure 13:
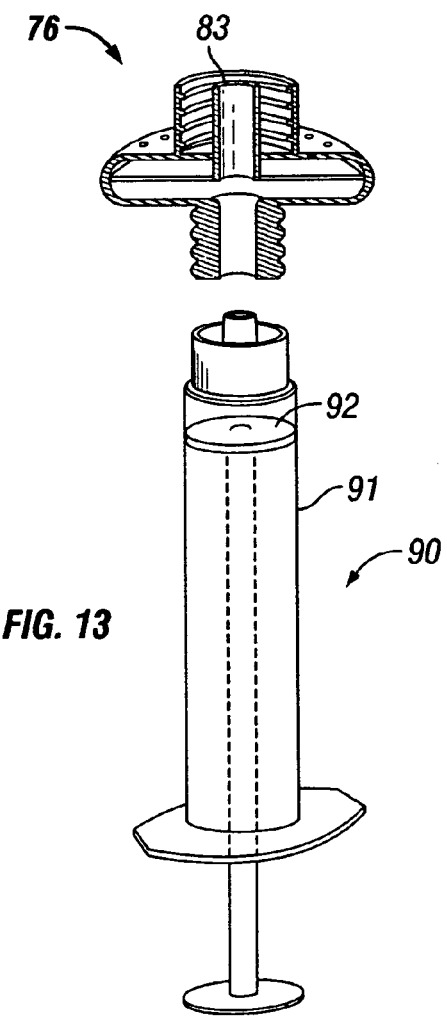
FIG. 13 is a longitudinal cross-sectional view of the blood collecting device illustrated in FIG. 12 illustrating removable insertion of a syringe to extract blood from a patient.

Referring next to FIG. 12 and FIG. 13, another embodiment the blood collecting device is characterized by a cap 76 including a cap housing 79 which is designed to removably fit on a syringe 90, having a syringe barrel 91 and a syringe plunger 92 slidably mounted therein. The cap 76 is similar in design to the blood collecting device 74 heretofore described with respect to FIG. 11, except lacks the cap base 77. The membrane cavity includes an upper air chamber 85a, which is sealed off from the blood flow tube 83, and a lower blood chamber 85b, which is disposed in fluid communication with the blood flow tube 83. A liquid impenetrable, air permeable membrane 86 separates the two chambers.

Figure 18:
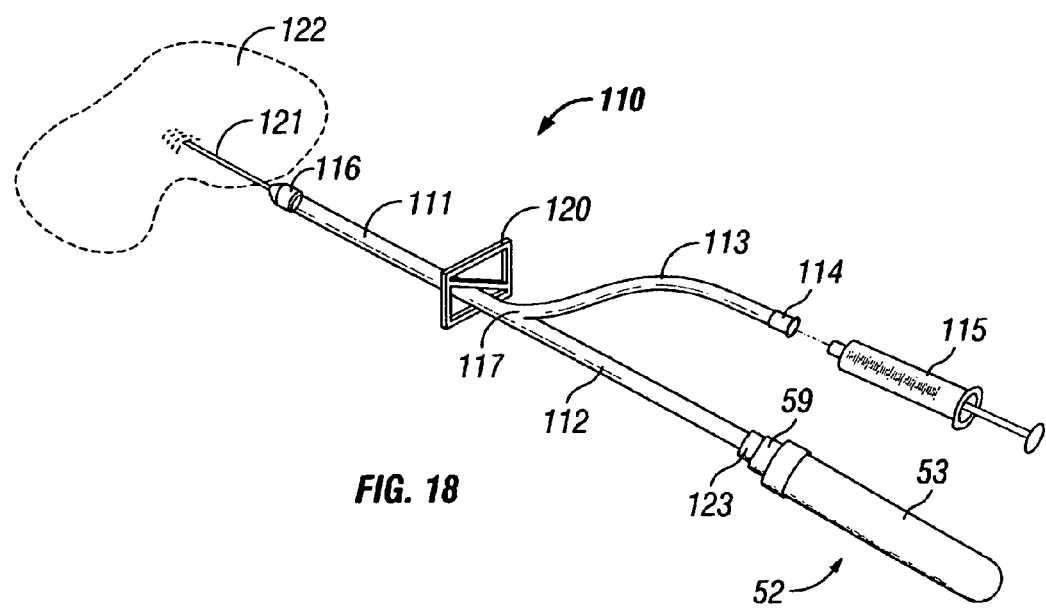
FIG. 18 is a perspective view of a bifurcated blood collection tubing, with the blood collecting device of FIG. 7 attached to the blood collection tubing in the collection of blood from a patient (in phantom)

Referring next to FIGS. 12, 13 and 18, in use of the blood collecting device 76, with the clamp 120 of the blood collection tubing 110 in the open position, the syringe 90 is inserted into the female luer 88, which may be a needle-less port. The male luer connector 84 is connected to the female needle-less port 123 (FIG. 18) of the blood collection tubing 110. The syringe plunger 92 is retracted from the syringe barrel 91 to draw blood from the patient 122; through the blood collection tubing 110 and blood flow tube 83, respectively, of the blood-collection device 76; and into the syringe barrel 91. Flowing from the blood flow tube 83, blood from the patient 122 collects in the blood chamber 85b to visually enable the blood collecting personnel to pull back on the syringe plunger 92 at a rate which accords with the rate of venous pressure blood flow from the patient 122. Furthermore, the air openings 82 in the upper housing plate 81 facilitate the flow of outside air through the air openings 82, the membrane 86, and into the syringe barrel 91, respectively, to prevent vacuum pressure from collapsing the patient's vein in the event that the syringe plunger 92 is pulled too quickly from the syringe barrel 91. If additional samples are needed, clamp 120 is closed, and a new syringe 90 is attached. After blood collection device 76 is removed, the tubing is then flushed as heretofore described of the blood collection device 52 in FIG. 9.

Referring next to FIGS. 14A and 15 of the drawings, still another embodiment of the blood collecting devices 93a illustrated in FIG. 14A includes a blood reservoir 94 having an elongated, generally cylindrical wall 95 through which extend multiple air slots 97 in a selected pattern. As illustrated in FIG. 15, which is a cross-section of the blood collecting device 93a of FIG. 14A, a membrane 96, which is air-permeable and liquid-impenetrable, lines the interior surfaces of the wall 95 and extends across the air slots 97. The membrane 96 may be oriented on the bottom, sides, top, or any combination thereof in the blood reservoir 94. A cap 98 is removably inserted in the mouth of the blood reservoir 94. A reagent 50 may be provided in the blood reservoir 94, in which case the cap 98 may be color-coded to indicate to personnel which reagent is contained in the blood reservoir 94 (purple for EDTA, green for heparin, etc.). The cross-sectional view of FIG. 15 illustrates how membrane 96 lines the inside reservoir 94, being revealed at air opening 97.

The blood collecting device 93a may be used in conjunction with a blood collection tubing 100 illustrated in FIG. 17 to collect blood from a patient 106. The blood collection tubing 100 may include a main tubing segment 101 having a male luer 105, which is inserted into a cannula 102, as heretofore described. A clamp 103 is typically provided in the main tubing segment 101. A blood collection tube holder or blood collection needle holder with the inserted blood collection needle (not illustrated), which may be conventional, is attached to a port 104 on the main tubing segment 101. The blood reservoir 94 is inserted in the blood collection tube holder. Upon opening of the main tubing segment 101 using the clamp 103, blood flows from the patient 106, through the main tubing segment 101 and into the blood reservoir 94, respectively. Simultaneously, air is forced from the blood reservoir 94 through the membrane 96 and air openings 97. Because the air openings 97 allow the internal pressure in the blood reservoir 94 to remain ambient, this facilitates flow of blood from the patient 106 to the blood reservoir 94 under venous pressure. After the desired sample of blood has been collected in the blood reservoir 94, the blood collection tube holder and blood collection needle (not shown) may be removed, and blood collection tubing 100 is flushed and used as ordinary extension tubing. It is understood that the blood collecting device 93a is capable of being used with the bifurcated blood collection tubing 110 of FIG. 18.

As illustrated in FIG. 14B, an alternative embodiment of the blood collecting device 93a includes multiple air openings 97a which replace the air slots 97 of FIG. 14A as extending through the wall 95 of the blood reservoir 94. The membrane 96 lines the interior surfaces of the wall 95 and spans the air openings 97a. Use of the blood collecting device 93b is as heretofore described with respect to the blood collecting device 93a of FIG. 14A.

Referring next to FIG. 16 and FIG. 1, it will be appreciated by those skilled in the art that with little modification, device 1 (FIGS. 1 and 2) and device 1a (FIG. 6) can be made to fit ordinary blood tube or needle holders. FIG. 16 illustrates this modification. Accordingly, the blood collecting device 99 includes a housing 2 having a housing wall 3, closed by a lower housing plate 6a and an upper housing plate 7 that defines a membrane cavity 8. At least one air opening 10 extends through the upper housing plate 7. A membrane 9, which is a liquid-impenetrable and air-permeable material, spans the housing wall 3 inside the membrane cavity 8. A male luer connector 12 extends from the upper housing plate 7. A blood flow tube 14 extends centrally through the male luer connector 12, the upper housing plate 7, the membrane cavity 8, the membrane 9 and the lower housing plate 6a. A typically threaded connector 11 extends downwardly from the lower housing plate 6a. A blood flow needle 15 extends through the threaded connector 11 and is provided in fluid communication with the blood flow tube 14. An air flow needle 16, having an air opening 17, is typically attached to the side of the blood flow needle 15. The cannulated tip of the air flow needle 16 extends beyond the cannulated tip of the blood flow needle 15. The upper end portion of the air flow needle 16 extends into the threaded connector 11 and is disposed in fluid communication with the membrane cavity 8 below the membrane 9. A self-sealing needle shield 18 is provided on the threaded connector 11 and normally covers the blood flow needle 15 and the air flow needle 16.

A blood tube/needle holder 130, which may be conventional, includes a generally elongated, cylindrical housing 132 having a housing wall 133 and a housing plate 136 which define a housing interior 135. An annular housing flange 134 typically extends outwardly from the bottom edge of the housing 132. An interiorly-threaded connector 11a extends downwardly from the housing plate 136, into the housing interior 135.

In use, as the threaded connector 11 is threaded into the interiorly-threaded connector 11a, the lower housing plate 6a and the housing plate 136 are brought into approximation. The blood-collecting device 99 then functions exactly as the blood-collecting devices 1 and 1a, as previously described with respect to FIGS. 1, 2 and 6. It is understood that the blood collecting device 1a heretofore described with respect to FIG. 6 could be modified for use with the blood tube or needle holder 130 illustrated in FIG. 16.

Figure 19:
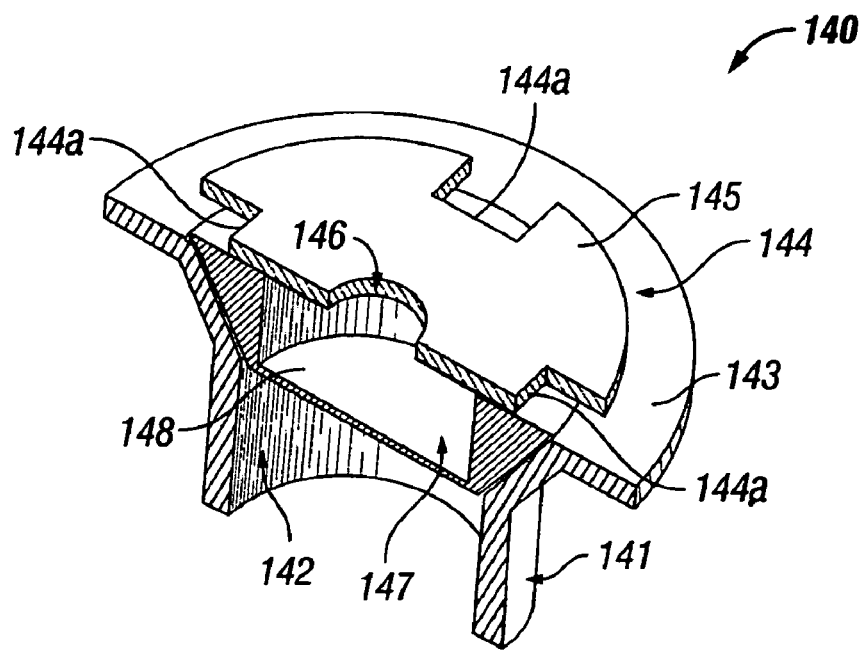
FIG. 19 is a perspective sectional view of a blood reservoir according to the present invention.

Referring next to FIG. 19 of the drawings, another embodiment of the blood collecting device according to the present invention is generally indicated by reference numeral 140. The blood collecting device 140 includes an elongated blood collecting chamber 141 (shown partially in section) which may be a standard or conventional syringe barrel having a luer connector element (not illustrated). The blood collecting chamber 141 includes a chamber interior 142 and is terminated by an outwardly-extending flange 143. An air vent 144, which is typically injection-molded, is inserted in the open end of the blood collecting chamber 141. The air vent 144 includes multiple slots 144a which facilitate spin-welding of the air vent 144 to the blood collecting chamber 141. A vent chamber 147 is provided in the air vent 144, and a vent opening 146 extends through the top of the vent insert 145 and communicates with the vent chamber 147. A membrane 148, which is typically air-permeable and liquid-impervious, separates the vent chamber 147 from the chamber interior 142. In fabrication of the blood collecting device 140, the membrane 148 is typically welded to the vent insert 145 before the vent insert 145 is spin-welded to the blood collecting chamber 141.

In typical use of the blood collecting device 140, the luer connector (not illustrated) of the blood collecting chamber 141 is initially connected to the female luer connector 123 on the collection tubing segment 112 of the blood collection tubing 110 illustrated in FIG. 18. After the catheter 121 is inserted in the patient 122, and the nale luer 116 of the blood collection tubing 110 is attached to hub of catheter 121, the clamp 120 is manipulated to the open position to establish flow of blood from the patient 122; through the catheter 121, main tubing segment 111, tubing bifurcation 117 and collection tubing segment 112, respectively; and into the chamber interior 142 of the blood collecting chamber 141. As the blood flows into the chamber interior 142, air is displaced from the chamber interior 142; through the membrane 148 and vent chamber 147, respectively; and out the vent opening 146 of the air vent 144. The membrane 148 prevents blood from exiting the air vent 144 through the vent opening 146. Next, a syringe 115 may be attached on the female port 114 of the blood collection tubing 110. Withdrawing on the plunger of the syringe 115 causes blood to flow from the blood collecting device 140 through the collection tubing segment 112, around tubing bifurcation 117, and collection tubing 113, respectively, and enter the syringe 115. Alternatively, a blood collection tube holder (not shown) may be attached at female port 114 and an evacuated tube (not shown) may be inserted to extract the blood from the blood collecting device 140. Sufficient blood must be in the blood collecting device 140 for a good sample to be obtained, or air will be pulled into the evacuated tube from the blood collecting device 140. After sufficient blood is collected, the clamp 120 is manipulated to the closed position and a syringe 115 filled with normal saline is attached to the female port 114. The tubing segment 113, tubing bifurcation 117 and tubing segment 112 are flushed with normal saline and the blood collecting device 140 is discarded. The clamp 120 is then opened and the tubing segment 111 flushed as the saline flows into the patient 122.

The syringe 115 is removed and the device 110 is used as ordinary extension tubing. It is understood that with little or no modification, the blood collecting chamber 141 may be a conventional syringe with the plunger removed.

Figure 20:
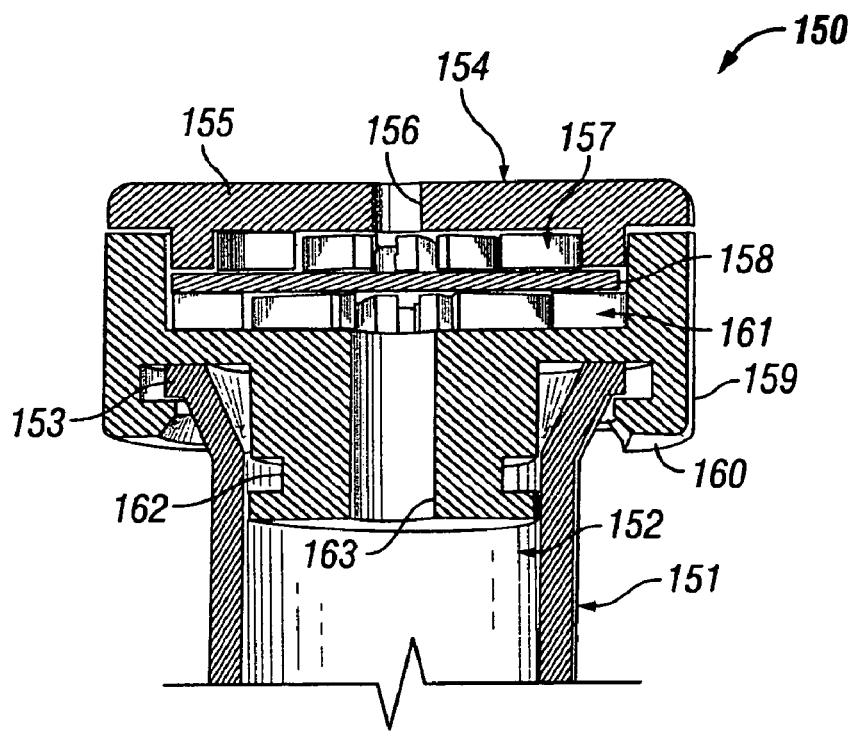
FIG. 20 is a perspective sectional view of an alternative blood reservoir according to the present invention.

Referring next to FIG. 20 of the drawings, an alternative embodiment of a blood collecting device (illustrated in longitudinal sectional view) according to the present invention is generally indicated by reference numeral 150. The blood collecting device 150 includes a blood collecting chamber 151 (shown partially in section) which may be a standard or conventional syringe barrel. The blood collecting chamber 151 has a chamber interior 152. A flange 153 extends outwardly from the open end of the blood collecting chamber 151. An air vent 154 is typically snapped into the open end of the blood collecting chamber 151 as will be hereinafter described. The air vent 154 typically includes an upper vent insert 155 and a lower vent insert 159 which is attached to the upper vent insert 155 typically using an ultrasonic welding technique. An air chamber 157 is provided in the upper vent insert 155, and a blood chamber 161 is provided in the lower vent insert 159. A central vent opening 156 extends through the upper vent insert 155, and a liquid-impervious and air-permeable membrane 158 spans the blood chamber 161 of the lower vent insert 159, beneath the vent opening 156. The membrane 158 separates the air chamber 157 from the blood chamber 161.

An insert flange 160 extends along the bottom of the lower vent insert 159 to facilitate removably snapping the air vent 154 onto the flange 153 of the blood collecting chamber 151. An O-ring groove 162 typically circumscribes the outer surface of the lower vent insert 159, beneath the blood chamber 161. An O-ring (not illustrated) is typically inserted in the O-ring groove 162 and provides a fluid-tight seal between the blood collecting chamber 151 and the lower vent insert 159. A central fluid opening 163 extends through the lower vent insert 159 and establishes fluid communication between the blood chamber 161 and the chamber interior 152 of the blood collecting chamber 151.

Use of the blood collecting device 150 is typically as was heretofore described with respect to the blood collecting device 140 of FIG. 19. Accordingly, as blood flows from the patient into the chamber interior 152, air is displaced from the chamber interior 152 and through the fluid opening 163, blood chamber 161, membrane 158 and air chamber 157, respectively, and is discharged through the vent opening 156. The blood is capable of flowing from the chamber interior 152, through the fluid opening 163 and into the blood chamber 161, respectively. The design of the blood collecting device 150 facilitates use of a membrane 158 having an enhanced surface area. Furthermore, the upper vent insert 155 and lower vent insert 159 can be made separately and snapped onto the blood collecting chamber 151 without use of a welding operation. It is understood that with little or no modification, the blood collecting chamber 151 may be a conventional syringe with the plunger removed.

While the preferred embodiments of the invention have been described above, it will be recognized and understood that various modifications can be made in the invention and the appended claims are intended to cover all such modifications which may fall within the spirit and scope of the invention.

Having described my invention with the particularity set forth above, I claim:

1. A blood-collecting device for a blood tube holder, comprising:

a disc-shaped housing comprising a membrane cavity;

an air-permeable and liquid-impervious membrane provided in said membrane cavity;

a blood flow tube extending through said membrane cavity and protruding through said membrane;

a blood flow conduit provided in fluid communication with and disposed in axially-aligned relationship with respect to said blood flow tube;

an air flow conduit carried by said blood flow conduit and having a first end provided in fluid communication with said membrane cavity, a second end spaced-apart from said first end and an air opening communicating with said air flow conduit between said first end and said second end;

a male luer connector extending from said housing and having a luer connector interior; and wherein said blood flow tube has a blunt tube end terminating in said luer connector interior of said male luer connector.

2. The blood collecting device of claim 1 further comprising a connector extending from said housing and wherein said blood flow conduit and said air flow conduit extend through said connector.

3. The blood collecting device of claim 2 further comprising a self-sealing needle shield extending from said connector and wherein said blood flow conduit and said air flow conduit extend into said self-sealing needle shield.

4. The blood-collecting device of claim 1 further comprising at least one air opening provided in said housing and communicating with said membrane cavity.

5. The blood collecting device of claim 1 further comprising an air opening provided in said air flow conduit.

6. A blood-collecting device for a blood tube holder, comprising:

a housing having a first surface and a second surface and comprising a membrane cavity;

an air-permeable and liquid-impervious membrane provided in said membrane cavity;

a male luer connector extending from said first surface of said housing;

blood flow tube extending from said first surface of said housing inside said male luer connector, through said membrane cavity and protruding through said membrane and having a blunt tube end terminating inside said male luer connector;

a threaded connector extending from said second surface of said housing;

an elongated blood flow conduit provided in fluid communication with and disposed in axially-aligned relationship with respect to said blood flow tube and extending through said threaded connector;

an elongated air flow conduit carried by said blood flow conduit and provided in fluid communication with said membrane cavity and extending from said threaded connector; and a self-sealing needle shield carried by said threaded connector and having an elongated, cylindrical needle shield interior containing said blood flow conduit and said air flow conduit.

* * * * *